(12) United States Patent
Yonekawa et al.

(10) Patent No.: US 7,227,052 B2
(45) Date of Patent: Jun. 5, 2007

(54) GFP EXPRESSION VECTOR LOCALIZED IN MITOCHONDRIA

(75) Inventors: Hiromichi Yonekawa, Saitama (JP); Hiroshi Shitara, Chiba (JP); Jun-ichi Miyazaki, Osaka (JP)

(73) Assignee: Tokyo Metropolitan Organization for Medical Research, Tokyo (JP)

( * ) Notice: Subject to any disclaimer, the term of this patent is extended or adjusted under 35 U.S.C. 154(b) by 0 days.

(21) Appl. No.: 10/473,637

(22) PCT Filed: Sep. 29, 2001

(86) PCT No.: PCT/JP01/08585

§ 371 (c)(1),
(2), (4) Date: Apr. 5, 2004

(87) PCT Pub. No.: WO02/079480

PCT Pub. Date: Oct. 10, 2002

(65) Prior Publication Data

US 2004/0154046 A1    Aug. 5, 2004

(30) Foreign Application Priority Data

Mar. 29, 2001  (JP) .............................. 2001-097102

(51) Int. Cl.
  *A01K 67/027*  (2006.01)
  *G01N 33/00*  (2006.01)
  *C12N 15/00*  (2006.01)
(52) U.S. Cl. ............................... 800/18; 800/3; 800/25
(58) Field of Classification Search ................... 800/3, 800/8, 18, 25
  See application file for complete search history.

(56) References Cited

FOREIGN PATENT DOCUMENTS

JP         2001-309736 A        11/2001

OTHER PUBLICATIONS

Rizzuto R, Chimeric green flourescent protein as a tool for visualizing subcellular organelles in living cells, 1005, Current Biology, vol. 5, pp. 635-642.*
Olson M, Mitochondria in apopotsis and human disease, 2001, Current Molecular Medicine, vol. 1, pp. 91-122. □□*
Yano M, Visualization of mitochondrial protein import in cultured mammalian cells with green flourescent protein and effects of overexpression of the human import receptor Tom20, JBC, 1997, vol. 272, pp. 8459-8465.*
Sun K, Role of mitochondria in cell apoptosis during hepatic ischemia-repurfusion injury and protective effect of ischemic postconditioning, 2004, World J Gastoenterol, vol. 10, pp. 1934-1938.*
Arden N, Life and death in mammalian cell culture: strategies for apoptosis inhibition, 2004, TIBS, vol. 22, pp. 174-180.*
Shitara H, Non-invasive visualization of sperm mitochondria behavior in transgenic mice with introduced green flourescent protein (GFP), 2001, FEBS, vol. 500, pp. 7-11.*
Ristevski S, Making better transgenic models, 2005, Molecular Biotechnology, vol. 29, pp. 153-163.*
Smith KR, Gene transfer in higher animals: theoretical considerations and key concepts, J. of Biotechnology, vol. 99, pp. 1-22.*
Houdebine LM, The methods to generate transgenic animals and to control transgene expression, 2002, J. of Biotechnology, vol. 98, pp. 145-160.□□*
Shitara et al., Generation and Application of Transgenic Mouse Having Mitochondria Visualized by Green Flourescent Protein Labeling, 72nd Annual Meeting of the Genetic Society of Japan, Program and Collection of Preliminary Reports, Sep. 30, 2000.
Shitara, H., et al., "Non-invasive visualization of sperm mitochondria behavior in transgenic mice with introduced green flourescent protein (GFP)", FEBS Letters, (Jun. 2001), vol. 500, No. 1-2, pp. 7-11.
Rizzuto, R., et al., "Double labelling of subcellular structures with organelle-targeted GFP mutants in vivo", Curr. Biol., (1998), vol. 6, No. 2, pp. 183-188.
Rizzuto, R., et al., "Chimeric green flourescent protein as a tool for visualizing subcellular organelles in living cells", Curr. Biol., (1995), vol. 5, No. 6, pp. 635-642.
Niwa, H., et al., "Efficient selection for high-expression transfectants with a novel eukaryotic vector", Gene, (1991), vol. 108, No. 2, pp. 193-199.
Ikawa, Masato, et al., "Hikaru Mouse!? Hakkou Owan Kurage no Idenshi wo Mouse de Hatsugen; Kouhan na Ouyou ni Kitai", Kagaku to Seibutsu, (1998), vol. 36, No. 3, pp. 140-141 (and English Translation).
Matsuyama, Shigemi, "Saibou-nai pH Henka to Apoptosis", Jikken Igaku, (2000), vol. 18, No. 14, pp. 1923-1926 (and English translation of the relevant parts thereof).
Barr, P.J., et al., "Apoptosis and Its Role in Human Disease", Bio/Technology, vol. 12, pp. 487-483, May 12, 1994.
Yuan, J., et al., "Apoptosis in the Nervous System", Nature, vol. 407, pp. 802-809, Oct. 12, 2000.
Gao, W., et al., "Temporal Relationship Between Cytochrome C Release and Mitochondrial Swelling During UV-Induced Apoptosis in Living HeLa Cells", Journal of Cell Science, vol. 114, pp. 2855-2862, May 2, 2001.
Frank, S., et al., "The Role of Dyamin-Related Protein 1, a Mediator of Mitochondrial Fission, in Apoptosis", Developmental Cell, vol. 1, pp. 515-525, Oct. 2001.

* cited by examiner

*Primary Examiner*—Sumesh Kaushal
*Assistant Examiner*—David Montanari
(74) *Attorney, Agent, or Firm*—Davidson, Davidson & Kappel, LLC

(57) ABSTRACT

A system for observing the behaviors of mitochondria during ontogeny and the dynamics of mitochondria in various tissues during pathological development is provided. A pCAGGS expression vector containing green fluorescent protein (GFP) gene and a transgenic animal characterized by expressing GFP specifically in mitochondria are provided.

6 Claims, 5 Drawing Sheets
(4 of 5 Drawing Sheet(s) Filed in Color)

Forelimbs of TG and WT mice immediately
after birth observed under a fluorescent microscope CLSM images of Tg mouse-derived fibroblasts

SEQUENCE LISTING

```
<160> NUMBER OF SEQ ID NOS: 10

<210> SEQ ID NO 1
<211> LENGTH: 38
<212> TYPE: DNA
<213> ORGANISM: Mus musculus

<400> SEQUENCE: 1
gcagaattct gcagcgccac catgccaagg ctcccccc                            38

<210> SEQ ID NO 2
<211> LENGTH: 52
<212> TYPE: DNA
<213> ORGANISM: Mus musculus

<400> SEQUENCE: 2
ggcggatcct aagcttgcat aatcaggaac atcataatgg gctttgggaa cc           52

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Primer for
      PCR

<400> SEQUENCE: 3
gatggatcca tcgccaccat ggtgagcaag                                     30

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Primer for
      PCR

<400> SEQUENCE: 4
cggaattctt acttgtacag ctcgtccatc cg                                  32
```

```
<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Primer for
      PCR

<400> SEQUENCE: 5
gctctagagc ctctgctaac c                                              21

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Primer for
      PCR

<400> SEQUENCE: 6
tgaacagctc ctcgcccttg ctc                                            23

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer for
      PCR

<400> SEQUENCE: 7
tgagcaaaga ccccaacgag aagc                                           24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Primer for
      PCR

<400> SEQUENCE: 8
ttagccagaa gtcagatgct caag                                           24

<210> SEQ ID NO 9
<211> LENGTH: 5630
<212> TYPE: DNA
<213> ORGANISM: Artificial Sequence
<220> FEATURE:
<223> OTHER INFORMATION: Description of Artificial Sequence: Expression
      Vector pCAGGS-COX8-EGFP
<220> FEATURE:
<221> NAME/KEY: transit_peptide
<222> LOCATION: (1737)..(1808)
<220> FEATURE:
<221> NAME/KEY: CDS
<222> LOCATION: (1851)..(2564)

<400> SEQUENCE: 9
gtcgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggact atttacggta aactgcccac ttggcagtac     240
atcaagtgta tcatatgcca agtacgcccc ctattgacgt caatgacggt aaatggcccg     300
```

-continued

```
cctggcatta tgcccagtac atgaccttat gggactttcc tacttggcag tacatctacg        360
tattagtcat cgctattacc atgggtcgag gtgagcccca cgttctgctt cactctcccc        420 atctccccc cctccccacc cccaattttg tatttattta tttttaatt attttgtgca          480 gcgatggggg cgggggggg ggggcgcgc gccaggcggg gcggggcggg gcgaggggcg          540
gggcggggcg aggcggagag gtgcggcggc agccaatcag agcggcgcgc tccgaaagtt        600
tccttttatg gcgaggcggc ggcggcggcg gccctataaa aagcgaagcg cgcggcgggc        660
gggagtcgct gcgttgcctt cgccccgtgc cccgctccgc gccgcctcgc gccgcccgcc        720
ccggctctga ctgaccgcgt tactcccaca ggtgagcggg cgggacggcc cttctcctcc        780
gggctgtaat tagcgcttgg tttaatgacg gctcgtttct tttctgtggc tgcgtgaaag        840
ccttaaaggg ctccgggagg gccctttgtg cgggggggag cggctcgggg ggtgcgtgcg        900
tgtgtgtgtg cgtggggagc gccgcgtgcg gcccgcgctg cccggcggct gtgagcgctg        960
cgggcgcggc gcgggctttt gtgcgctccg cgtgtgcgcg aggggagcgc ggccgggggc       1020
ggtgccccgc ggtgcggggg ggctgcgagg ggaacaaagg ctgcgtgcgg ggtgtgtgcg       1080 tggggggtg agcaggggggt gtgggcgcgg cggtcgggct gtaaccccccc cctgcacccc       1140 cctcccgag ttgctgagca cggcccggct tcgggtgcgg ggctccgtgc ggggcgtggc       1200
gcggggctcg ccgtgccggg cgggggtgg cggcaggtgg gggtgccggg cggggcgggg       1260
ccgcctcggg ccggggaggg ctcgggggag gggcgcggcg gccccggagc gccggcggct       1320
gtcgaggcgc ggcgagccgc agccattgcc ttttatggta atcgtgcgag agggcgcagg       1380
gacttccttt gtcccaaatc tggcggagcc gaaatctggg aggcgccgcc gcacccctc       1440 tagcgggcgc gggcgaagcg gtgcggcgcc ggcaggaagg aaatgggcgg ggagggcctt       1500
cgtgcgtcgc cgcgccgccg tccccttctc catctccagc ctcggggctg ccgcaggggg       1560
acggctgcct tcggggggga cggggcaggg cggggttcgg cttctggcgt gtgaccggcg       1620
gctctagagc ctctgctaac catgttcatg ccttcttctt tttcctacag ctcctgggca       1680
acgtgctggt tgttgtgctg tctcatcatt ttggcaaaga attctgcagc gccaccatgc       1740
caaggctccc ccctatcctg cggctgctcc aagcgcctgc gaagttcaca gtggttccca       1800
aagcccatta tgatgttcct gattatgcaa gcttaggatc catcgccacc atg gtg         1856
                                                              Met Val
                                                               1
```

| agc aag ggc gag gag ctg ttc acc ggg gtg gtg ccc atc ctg gtc gag | 1904 |
|---|---|
| Ser Lys Gly Glu Glu Leu Phe Thr Gly Val Val Pro Ile Leu Val Glu | |
| 5 10 15 | |

| ctg gac ggc gac gta aac ggc cac aag ttc agc gtg tcc ggc gag ggc | 1952 |
|---|---|
| Leu Asp Gly Asp Val Asn Gly His Lys Phe Ser Val Ser Gly Glu Gly | |
| 20 25 30 | |

| gag ggc gat gcc acc tac ggc aag ctg acc ctg aag ttc atc tgc acc | 2000 |
|---|---|
| Glu Gly Asp Ala Thr Tyr Gly Lys Leu Thr Leu Lys Phe Ile Cys Thr | |
| 35 40 45 50 | |

| acc ggc aag ctg ccc gtg ccc tgg ccc acc ctc gtg acc acc ctg acc | 2048 |
|---|---|
| Thr Gly Lys Leu Pro Val Pro Trp Pro Thr Leu Val Thr Thr Leu Thr | |
| 55 60 65 | |

| tac ggc gtg cag tgc ttc agc cgc tac ccc gac cac atg aag cag cac | 2096 |
|---|---|
| Tyr Gly Val Gln Cys Phe Ser Arg Tyr Pro Asp His Met Lys Gln His | |
| 70 75 80 | |

| gac ttc ttc aag tcc gcc atg ccc gaa ggc tac gtc cag gag cgc acc | 2144 |
|---|---|
| Asp Phe Phe Lys Ser Ala Met Pro Glu Gly Tyr Val Gln Glu Arg Thr | |
| 85 90 95 | |

| | | | | | | | | | | | | | | | | |
|---|---|---|---|---|---|---|---|---|---|---|---|---|---|---|---|---|
| atc | ttc | ttc | aag | gac | gac | ggc | aac | tac | aag | acc | cgc | gcc | gag | gtg | aag | 2192 |
| Ile | Phe | Phe | Lys | Asp | Asp | Gly | Asn | Tyr | Lys | Thr | Arg | Ala | Glu | Val | Lys | |
| | 100 | | | | 105 | | | | | 110 | | | | | | |
| ttc | gag | ggc | gac | acc | ctg | gtg | aac | cgc | atc | gag | ctg | aag | ggc | atc | gac | 2240 |
| Phe | Glu | Gly | Asp | Thr | Leu | Val | Asn | Arg | Ile | Glu | Leu | Lys | Gly | Ile | Asp | |
| 115 | | | | | 120 | | | | | 125 | | | | | 130 | |
| ttc | aag | gag | gac | ggc | aac | atc | ctg | ggg | cac | aag | ctg | gag | tac | aac | tac | 2288 |
| Phe | Lys | Glu | Asp | Gly | Asn | Ile | Leu | Gly | His | Lys | Leu | Glu | Tyr | Asn | Tyr | |
| | | | | 135 | | | | | 140 | | | | | 145 | | |
| aac | agc | cac | aac | gtc | tat | atc | atg | gcc | gac | aag | cag | aag | aac | ggc | atc | 2336 |
| Asn | Ser | His | Asn | Val | Tyr | Ile | Met | Ala | Asp | Lys | Gln | Lys | Asn | Gly | Ile | |
| | | | 150 | | | | | 155 | | | | | 160 | | | |
| aag | gtg | aac | ttc | aag | atc | cgc | cac | aac | atc | gag | gac | ggc | agc | gtg | cag | 2384 |
| Lys | Val | Asn | Phe | Lys | Ile | Arg | His | Asn | Ile | Glu | Asp | Gly | Ser | Val | Gln | |
| | | 165 | | | | | 170 | | | | | 175 | | | | |
| ctc | gcc | gac | cac | tac | cag | cag | aac | acc | ccc | atc | ggc | gac | ggc | ccc | gtg | 2432 |
| Leu | Ala | Asp | His | Tyr | Gln | Gln | Asn | Thr | Pro | Ile | Gly | Asp | Gly | Pro | Val | |
| | 180 | | | | | 185 | | | | | 190 | | | | | |
| ctg | ctg | ccc | gac | aac | cac | tac | ctg | agc | acc | cag | tcc | gcc | ctg | agc | aaa | 2480 |
| Leu | Leu | Pro | Asp | Asn | His | Tyr | Leu | Ser | Thr | Gln | Ser | Ala | Leu | Ser | Lys | |
| 195 | | | | | 200 | | | | | 205 | | | | | 210 | |
| gac | ccc | aac | gag | aag | cgc | gat | cac | atg | gtc | ctg | ctg | gag | ttc | gtg | acc | 2528 |
| Asp | Pro | Asn | Glu | Lys | Arg | Asp | His | Met | Val | Leu | Leu | Glu | Phe | Val | Thr | |
| | | | | 215 | | | | | 220 | | | | | 225 | | |
| gcc | gcc | ggg | atc | act | ctc | ggc | atg | gac | gag | ctg | tac | aagtaagaat | | | | 2574 |
| Ala | Ala | Gly | Ile | Thr | Leu | Gly | Met | Asp | Glu | Leu | Tyr | | | | | |
| | | | 230 | | | | | 235 | | | | | | | | |

```
tcactcctca ggtgcaggct gcctatcaga aggtggtggc tggtgtggcc aatgccctgg    2634
ctcacaaata ccactgagat ctttttccct ctgccaaaaa ttatggggac atcatgaagc    2694
cccttgagca tctgacttct ggctaataaa ggaaatttat tttcattgca atagtgtgtt    2754
ggaattttt gtgtctctca ctcggaagga catatgggag ggcaaatcat ttaaaacatc    2814
agaatgagta tttggtttag agtttggcaa catatgccat atgctggctg ccatgaacaa    2874
aggtggctat aaagaggtca tcagtatatg aaacagcccc ctgctgtcca ttccttattc    2934
catagaaaag ccttgacttg aggttagatt ttttttatat tttgttttgt gttattttt    2994
tctttaacat ccctaaaatt ttccttacat gttttactag ccagattttt cctcctctcc    3054
tgactactcc cagtcatagc tgtccctctt ctcttatgaa gatccctcga cctgcagccc    3114
aagcttggcg taatcatggt catagctgtt tcctgtgtga aattgttatc cgctcacaat    3174
tccacacaac atacgagccg gaagcataaa gtgtaaagcc tggggtgcct aatgagtgag    3234
ctaactcaca ttaattgcgt tgcgctcact gcccgctttc cagtcgggaa acctgtcgtg    3294
ccagcggatc cgcatctcaa ttagtcagca accatagtcc cgcccctaac tccgcccatc    3354
ccgcccctaa ctccgcccag ttccgcccat tctccgcccc atggctgact aattttttt    3414
atttatgcag aggccgaggc cgcctcggcc tctgagctat tccagaagta gtgaggaggc    3474
ttttttggag gcctaggctt ttgcaaaaag ctaacttgtt tattgcagct tataatggtt    3534
acaaataaag caatagcatc acaaatttca caaataaagc atttttttca ctgcattcta    3594
gttgtggttt gtccaaactc atcaatgtat cttatcatgt ctggatccgc tgcattaatg    3654
aatcggccaa cgcgcgggga gaggcggttt gcgtattggg cgctcttccg cttcctcgct    3714
cactgactcg ctgcgctcgg tcgttcggct gcggcgagcg gtatcagctc actcaaaggc    3774
ggtaatacgg ttatccacag aatcagggga taacgcagga aagaacatgt gagcaaaagg    3834
ccagcaaaag gccaggaacc gtaaaaaggc cgcgttgctg gcgtttttcc ataggctccg    3894
```

-continued

```
cccccctgac gagcatcaca aaaatcgacg ctcaagtcag aggtggcgaa acccgacagg    3954
actataaaga taccaggcgt ttccccctgg aagctccctc gtgcgctctc ctgttccgac    4014
cctgccgctt accggatacc tgtccgcctt tctcccttcg ggaagcgtgg cgctttctca    4074
atgctcacgc tgtaggtatc tcagttcggt gtaggtcgtt cgctccaagc tgggctgtgt    4134
gcacgaaccc cccgttcagc ccgaccgctg cgccttatcc ggtaactatc gtcttgagtc    4194
caacccggta agacacgact tatcgccact ggcagcagcc actggtaaca ggattagcag    4254
agcgaggtat gtaggcggtg ctacagagtt cttgaagtgg tggcctaact acggctacac    4314
tagaaggaca gtatttggta tctgcgctct gctgaagcca gttaccttcg aaaaagagt    4374
tggtagctct tgatccggca acaaaccac cgctggtagc ggtggttttt ttgtttgcaa    4434
gcagcagatt acgcgcagaa aaaaggatc tcaagaagat cctttgatct tttctacggg    4494
gtctgacgct cagtggaacg aaaactcacg ttaagggatt ttggtcatga gattatcaaa    4554
aaggatcttc acctagatcc ttttaaatta aaatgaagt tttaaatcaa tctaaagtat    4614
atatgagtaa acttggtctg acagttacca atgcttaatc agtgaggcac ctatctcagc    4674
gatctgtcta tttcgttcat ccatagttgc ctgactcccc gtcgtgtaga taactacgat    4734
acgggagggc ttaccatctg gccccagtgc tgcaatgata ccgcgagacc cacgctcacc    4794
ggctccagat ttatcagcaa taaaccagcc agccggaagg gccgagcgca gaagtggtcc    4854
tgcaacttta tccgcctcca tccagtctat taattgttgc cgggaagcta gagtaagtag    4914
ttcgccagtt aatagtttgc gcaacgttgt tgccattgct acaggcatcg tggtgtcacg    4974
ctcgtcgttt ggtatggctt cattcagctc cggttcccaa cgatcaaggc gagttacatg    5034
atcccccatg ttgtgcaaaa aagcggttag ctccttcggt cctccgatcg ttgtcagaag    5094
taagttggcc gcagtgttat cactcatggt tatggcagca ctgcataatt ctcttactgt    5154
catgccatcc gtaagatgct tttctgtgac tggtgagtac tcaaccaagt cattctgaga    5214
atagtgtatg cggcgaccga gttgctcttg cccggcgtca atacgggata ataccgcgcc    5274
acatagcaga actttaaaag tgctcatcat tggaaaacgt tcttcgggc gaaaactctc    5334
aaggatctta ccgctgttga atccagttc gatgtaaccc actcgtgcac ccaactgatc    5394
ttcagcatct tttactttca ccagcgtttc tgggtgagca aaaacaggaa ggcaaaatgc    5454
cgcaaaaaag gaataaggg cgacacggaa atgttgaata ctcatactct ccttttttca    5514
atattattga agcatttatc agggttattg tctcatgagc ggatacatat ttgaatgtat    5574
ttagaaaaat aaacaaatag gggttccgcg cacatttccc cgaaaagtgc cacctg       5630
```

<210> SEQ ID NO 10
<211> LENGTH: 238
<212> TYPE: PRT
<213> ORGANISM: Artificial Sequence
<220> FEATURE:
<223> OTHER INFORMATION: Description of Artificial Sequence: Aequorea
      victoria EGFP coding region modified for codon optimization

<400> SEQUENCE: 10

```
Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45
```

```
-continued

Cys Thr Thr Gly Lys Leu Pro Val Pro Trp Pro Thr Leu Val Thr Thr
    50              55              60

Leu Thr Tyr Gly Val Gln Cys Phe Ser Arg Tyr Pro Asp His Met Lys
65              70              75              80

Gln His Asp Phe Phe Lys Ser Ala Met Pro Glu Gly Tyr Val Gln Glu
            85              90              95

Arg Thr Ile Phe Phe Lys Asp Asp Gly Asn Tyr Lys Thr Arg Ala Glu
            100             105             110

Val Lys Phe Glu Gly Asp Thr Leu Val Asn Arg Ile Glu Leu Lys Gly
        115             120             125

Ile Asp Phe Lys Glu Asp Gly Asn Ile Leu Gly His Lys Leu Glu Tyr
    130             135             140

Asn Tyr Asn Ser His Asn Val Tyr Ile Met Ala Asp Lys Gln Lys Asn
145             150             155             160

Gly Ile Lys Val Asn Phe Lys Ile Arg His Asn Ile Glu Asp Gly Ser
            165             170             175

Val Gln Leu Ala Asp His Tyr Gln Gln Asn Thr Pro Ile Gly Asp Gly
            180             185             190

Pro Val Leu Leu Pro Asp Asn His Tyr Leu Ser Thr Gln Ser Ala Leu
        195             200             205

Ser Lys Asp Pro Asn Glu Lys Arg Asp His Met Val Leu Leu Glu Phe
    210             215             220

Val Thr Ala Ala Gly Ile Thr Leu Gly Met Asp Glu Leu Tyr
225             230             235
```

GFP EXPRESSION VECTOR LOCALIZED IN MITOCHONDRIA

The following application is a 371 of PCT/JP01/08585 which claims priority form JAPAN 2001-97102.

FIELD OF THE INVENTION

The present invention relates to a mitochondria-localized GFP expression vector, by which an introduced green fluorescent protein (GFP) gene is expressed locally in mitochondria, and a transgenic animal that expresses GFP specifically in mitochondria.

BACKGROUND OF THE INVENTION

Mitochondrial DNA (mtDNA) is known to show strict maternal inheritance in mammals. We have previously found that sperm mtDNA was eliminated from the cytoplasm of embryonic cells by the 2-cell-stage in early embryogenesis, using highly sensitive PCR methods (Kaneda, H. et al., (1995) Proc. Natl. Acad. Sci. USA 92, 4542–4546; and Shitara, H. et al., (1998) Genetics 148, 851–857). This phenomenon could cause the maternal inheritance of mtDNA.

To observe directly and visually the intracellular behavior of sperm mitochondria during early embryogenesis, mitochondrial fraction, cells and tissue have been stained by Rhodamine 123 or by MitoTracker (Molecular Probes, OR; cat. M7512) and observed under a fluorescence microscope (Kaneda, H. et al., (1995) Proc. Natl. Acad. Sci. USA 92, 4542–4546; Cummins, J. M. et al., (1997) Zygote 5, 301–308; Sutovsky, P. et al., (1996) Biol. Reprod. 55, 1195–1205; and Sutovsky, P. et al., (2000) Biol. Reprod. 63, 582–590). Using these fluorescent dyes, mitochondria can be clearly and specifically stained in the middle piece of a sperm cell.

However, several drawbacks are known regarding the above methods. The above dyes are easily bleached under the irradiation of UV light, and even without irradiation of UV light the dyes rapidly become bleached. The procedures involved in the staining such as centrifugation and resuspension damaged cells and mitochondria, and consequently the fertility of sperm is remarkably reduced, and the dyes are easily released after staining. These drawbacks make it difficult to conduct sequential or repeated observations of mitochondria.

Instead of vital staining dyes, the use of green fluorescent protein (GFP), which has been widely applied as a noninvasive chemiluminescent reporter molecule, enables the visualization of the localization and/or migration of proteins of interest in intracellular compartmentation. GFP can also be used for real-time visualization of intracellular organelles. In particular, Rizzuto et al. (Rizzuto, R. et al., (1995) Curr. Biol. 5, 635–642; and Rizzuto, R. et al., (1996) Curr. Biol. 6, 183–188) reported that GFP was accumulated exclusively in the mitochondria of HeLa cells by transfection of a GFP cDNA clone linked with a polynucleotide encoding the N-terminus of the mitochondrial cytochrome c oxidase subunit VIII precursor protein (mtGFP). Fluorescence was observed as a rod-like shape typical of mitochondria, suggesting that GFP is accumulated in mitochondria. Moreover, the reduction of GFP fluorescence was not at all or less observed by repeated UV-irradiation, whereas the fluorescence of rhodamine 123, a vital staining dye specific to mitochondria, was dramatically reduced under the same conditions.

As described above, it has been expected that GFP linked with an importing signal to a certain organelle has wide applications in real-time observation of the intracellular organelle.

However, the above methods have drawbacks in that applicable cells are limited to cells such as established cultured cells and cells of tissue that can be subjected to primary culture, and that the behavior of mitochondria during ontogenesis and the dynamics of mitochondria in lesions during pathological development cannot be observed.

To express mitochondria-localized GFP in every tissue in an individual animal, an appropriate vector must be selected. To date, expression vectors having promoter sequences to enable tissue-specific expression or vectors that enable expression in all the tissues have been invented and improved. However, there are only few expression vectors that are completely sufficient, particularly in terms of the expression level of a foreign gene.

In the meantime, apoptosis, which is also referred to as programmed cell death and by which the cell content is not released outside the cell, in contrast to necrosis by which the cell content is released extracellularly, is known to cause disorders of mitochondria involving characteristic morphological changes such as the aggregation or fragmentation of nuclei within cells and the discharge of cytochrome C. Recently, the involvement of apoptosis in ontogeny and various diseases is increasingly reported. However, most of the facts about apoptosis remained unknown.

SUMMARY OF THE INVENTION

As a result of a variety of studies undertaken to solve the above problems, we have selected a pCAGGS expression vector, which enables strong expression of a foreign gene in every tissue. We have further constructed a mitochondria-localized GFP expression vector to label mitochondria using GFP, and generated as well a transgenic (Tg) animal having mitochondria visualized by GFP.

That is, the present invention provides the following (1) to (11):

(1) A mitochondria-localized GFP expression vector, which is a pCAGGS expression vector containing a green fluorescent protein (GFP) gene, wherein the GFP is locally expressed in mitochondria.

(2) The expression vector of (1) above, which has an importing signal sequence to mitochondria.

(3) The expression vector of (2) above, wherein the importing signal sequence is the signal sequence of cytochrome c oxidase subunit VIII.

(4) A mitochondria-localized GFP expression vector, which is an expression vector containing a GFP gene, wherein the GFP is locally expressed in mouse mitochondria.

(5) A transgenic animal, wherein the expression vector of any one of (1) to (4) above has been introduced.

(6) A transgenic animal, wherein GFP is expressed specifically in mitochondria.

(7) The transgenic animal of (6) above, wherein a gene for an importing signal to mitochondria and a GFP gene have been introduced.

(8) A cell having the expression vector of any one of (1) to (4) above introduced.

(9) A tissue or cell derived from the transgenic animal of any one of (5) to (7) above.

(10) A screening method for an inducer of a disorder of mitochondria or apoptosis, comprising the steps of:

(a) contacting the transgenic animal of any one of (5) to (7) above or the cell of (8) or (9) above with a test substance; and
(b) confirming whether or not a disorder of mitochondria or apoptosis is induced.

(11) A screening method for an apoptosis suppressor, comprising the steps of:
(a) contacting the transgenic animal of any one of (5) to (7) above, or the cell of (8) or (9) above with a test substance;
(b) treating the above animal or the above cell with the apoptosis inducer; and
(c) confirming whether or not apoptosis is suppressed.

The present invention will be described in detail as follows.

The green fluorescent protein (GFP) used in the present invention may be any protein that is used in the art. A genetically modified GFP having enhanced fluorescence intensity or having fluorescence that disappears within a certain period of time can also be used. Examples of a commercially available GFP product include pEGFP and pEGFP-N1/2/3 (CLONTECH, cat.#6077, K6001-1). As described above, GFP has the excellent features that it is noninvasive and that it is not bleached by UV irradiation or the like.

Any vector that is used in the art can be appropriately used as an expression vector that can be used in the present invention. Specifically, the expression vector may be selected according to the types, etc. of cells or animals for the above GFP gene to be introduced, and is not specifically limited. The pCAGGS expression vector (Niwa, B. et al., (1991) Gene 108, 193–200), which has no tissue specificity and by which strong expression can be expected, can be preferably used. Further, when a gene is introduced into a cell or an animal, the expression vector may be introduced intact, or a target gene may also be introduced after preparation of an expression cassette containing the target gene. The introduction method may be appropriately selected according to the cell or animal to which a gene is to be introduced. Therefore, the "expression vector" in the present specification also includes the above expression cassette.

For the introduced GFP to be expressed locally and specifically in mitochondria, for example, an expression vector preferably has an importing signal sequence to mitochondria on the upstream side of the GFP gene. Examples of the importing signal sequence include that of cytochrome c oxidase subunit VIII, and cDNA of cytochrome C. The GFP gene and the above importing signal sequence may be adjacent to each other or separated from each other by several tens of nucleotides, but the reading frames must be the same.

In addition, the expression vector of the present invention may contain regulatory sequences such as a promoter and a terminator, and a tag such as HA1 for appropriately regulating the expression of the gene to be introduced.

The transgenic animal of the present invention is characterized in that GFP is specifically expressed in mitochondria, and in particular the above expression vector has been introduced.

Examples of the types of animals used herein may be any animals other than humans, and include, but are not limited to, mammals such as a mouse, rat, hamster, guinea pig, rabbit, pig, miniature pig, cattle, sheep, cat and dog, birds such as a chicken, fish, insects such as drosophila and nematodes. In the present invention, the animal is preferably a rodent, and particularly preferably a mouse in terms of feeding and operation.

For example, the transgenic animal of the present invention can be generated as described below. First, an expression vector is constructed as described above, an expression cassette is excised from the expression vector by cleavage using restriction enzymes or the like, and then the expression cassette is introduced into totipotent cells. Examples of totipotent cells that can be used herein include fertilized eggs, early embryos and embryonic stem cells (ES cells). Introduction into totipotent cells can be performed by techniques that are normally employed in the art such as an electrostatic pulse method, a liposome method, a calcium phosphate method or a microinjection method.

The above-treated totipotent cells are transplanted in the oviduct of a pseudo-parent to produce progenies. Then animals having GFP gene are selected from the progenies. Whether or not animals have GFP gene can be confirmed by any conventional method such as Southern blotting or PCR using a GFP gene-specific probe or primers. In the present invention, it can also be determined by visually observing the expressed GFP.

The present invention also provides a cell, wherein the above mitochondria-localized GFP expression vector has been introduced.

The cells of the present invention are not limited to those derived from the above transgenic animal, and may be any cells of eukaryotes having mitochondria. Examples of the cell include those of a plant, yeast, and drosophila. The expression vector of the present invention can be introduced into these cells by techniques that are normally employed in the art.

Fluorescence originating from GFP is localized in the mitochondria of the transgenic animal, tissue and cells of the present invention and is specifically expressed. Hence, the use of the transgenic animal of the present invention enables noninvasive observation of, for example, the state of sperm mitochondria during early embryogenesis. Fluorescence of the transgenic animal of the present invention is strong and stable, so that repeated observation under a confocal laser scanning microscope can be conducted.

As described above, GFP expression is localized in mitochondria of the transgenic animal according to the present invention. However, the localized area is changed to the whole cytoplasm by treatment with an inducer of a disorder of mitochondria, apoptosis or the like. We have confirmed that the GFP localization pattern is changed by the inducer of a disorder of mitochondria or apoptosis, using cells obtained from the transgenic animal of the present invention. Specifically, the determination of GFP localization using the transgenic animal or the cells of the present invention makes it possible to easily determine whether or not apoptosis occurs. For example, the transgenic animal of the present invention can be used as a model animal to study the mechanism, etc. of apoptosis.

Moreover, there are many known cases where the involvement of a disorder of mitochondria (including apoptosis) in the pathological development and progress of various diseases is assumed. Thus, various pathological models (brain ischemia model, cardiac muscle ischemia model and the like) are prepared using the transgenic animal obtained by the present invention, so as to be able to know the sites and the degrees of disorders of mitochondria in various pathological conditions, elucidate the pathological conditions and characterize the models. Further, the use of the transgenic animal according to the present invention or cells derived from the transgenic animal enables screening for suppressors, inducers or the like of disorders of mitochondria.

Specifically, a test substance is allowed to come into contact with the transgenic animal or the cell of the present invention to confirm whether or not a disorder of mitochondria or apoptosis is induced, so that screening for an inducer of the disorder of mitochondria or apoptosis can be performed.

Moreover, using a conventionally known apoptosis inducer such as staurosporine, a Fas antibody or an apoptosis inducer obtained by the above screening, an apoptosis suppressor can also be screened for by contacting a test substance with the transgenic animal or the cell of the present invention, and then treating with the apoptosis inducer to confirm whether or not apoptosis has been suppressed.

By the use of the transgenic animal or the cell of the present invention, the induction and the suppression of apoptosis can be easily known visually due to the fluorescence of GFP. In the above screening method, to confirm the induction or the suppression of apoptosis, preferably, a comparison with a control animal or a control cell under the same conditions except for a lack of contact with the above test substance may be performed. Alternatively a comparison with the states before the contact with the test substance or the state before the treatment using an apoptosis inducer are preferably performed.

In the above screening method, the test substance is not specifically limited. Examples of the test substance include a peptide, a protein, a non-peptide compound, a synthetic compound, a fermentation product and a cell extract.

In the above screening method, a test substance may be caused to come into contact in vitro when the cells are used. When the transgenic animal is used, any conventionally known method of local or systemic administration may be employed, including oral administration or parenteral administration such as subcutaneous injection or intraperitoneal injection. Such the administration methods can be appropriately selected according to the types of animals used, pathological conditions, the presence or the absence of target tissue and the like.

The apoptosis inducer obtained by the above screening method can be used for, for example, therapies against cell proliferative diseases such as cancer. In addition, the apoptosis suppressor obtained by the above screening method can be used for, for example, therapies against diseases caused by cell death such as Alzheimer's disease or ischemic disease.

BRIEF DESCRIPTION OF THE DRAWINGS

The patent or application file contains at least one drawing executed in color. Copies of this patent or patent application publication with color drawings will be provided by the Office upon request and payment of the necessary fee.

The patent or application file contains at least one drawing executed in color. Copies of this patent or patent application publication with color drawings will be provided by the Office upon request and payment of the necessary fee.

BEST MODE OF CARRYING OUT THE INVENTION

EXAMPLE 1

Construction of Expression Vector

The signal sequence of cytochrome c oxidase subunit VIII (COX8, GeneBank U15541) was amplified by PCR reaction using primers, 5'-GCA GAA TTC TGC AGC GCC ACC ATG CCA AGG CTC CCC CC-3' (SEQ ID NO: 1) and 5'-GGC GGA TCC TAA GCT TGC ATA ATC AGG AAC ATC ATA ATG GGC TTT GGG AAC C-3' (SEQ ID NO: 2) and C57BL/6J(B6)-derived genomic DNA as a template. In this case, the primer of SEQ ID NO: 2 contained the nucleotide sequence of HA1 (TAA GCT TGC ATA ATC AGG AAC ATC ATA: nucleotide Nos. 10 to 36 of SEQ ID NO: 2). Therefore, the HA1 nucleotide sequence was incorporated in the amplification product obtained by the PCR reaction. The coding region of EGFP (SEQ ID NO: 10) was amplified by PCR reaction using primers, 5'-GAT GGA TCC ATC GCC ACC ATG GTG AGC AAG-3' (SEQ ID NO: 3) and 5'-CGG AAT TCT TAC TTG TAC AGC TCG TCC ATC CG-3' (SEQ ID NO: 4) and a recombinant plasmid pEGFP-N3 (Clontech, Calif.) as a template. Both PCR products were cleaved with EcoR I and BamH I and ligated into a pCAGGS expression vector (Niwa, B. et al., (1991) Gene 108, 193–200) that had been cleaved with EcoR I.

Figure 1:
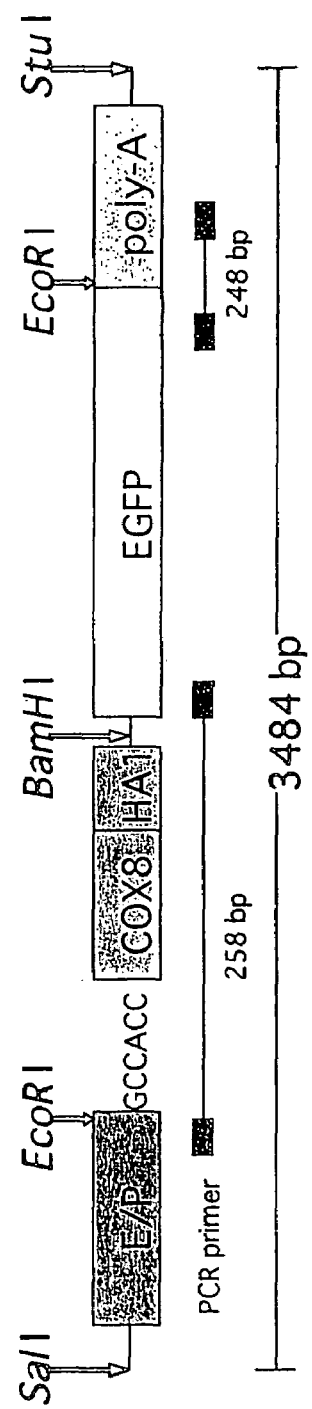
FIG. 1 shows an example of the mitochondria-localized GFP expression vector of the present invention.

The structure of the main portion of the expression vector constructed by the above procedures is shown in FIG. 1, and the entire sequence is shown in SEQ ID NO: 9.

EXAMPLE 2

Generation of Transgenic Mouse

DNA fragments to be used for the generation of a transgenic animal were obtained by double digestion using Sal I and Stu I (FIG. 1), separated by agarose gel electrophoresis from the cloning vector, and then purified by QIAEX II (QIAGEN, Calif.). The purified DNA fragments were injected into the pronuclei of fertilized mouse (B6) oocytes according to the standard procedure (Hogan, B. et al., (1994) Manipulating the Mouse Embryo 2nd edn., Cold Spring Harbor Laboratory Press, Cold Spring Harbor, N.Y.). To identify transgenic mice, genomic DNA was prepared from ear-punched pieces. Specifically, the punched pieces were incubated overnight at 37° C. in a PCR buffer/nonionic surfactant and proteinase K (50 mM KCl, 10 mM Tris-HCl, (pH 8), 1.5 mM $MgCl_2$, 0.1% gelatine, 0.45% NP-40, 0.45% Tween-20 and 100 μg/ml proteinase K). To inactivate protein kinase K, incubation was performed at 95° C. for 15 minutes. The obtained solution was used as a DNA sample.

Figure 2:
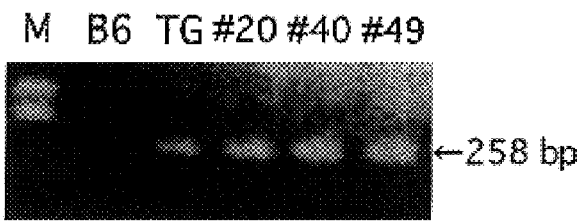
FIG. 2 is a photograph showing the detection of a transgene by the PCR method. M: marker (φx174/Hae III digest), B6: B6-derived total DNA, TG: B6-derived total DNA and a transgene (Sal I/Stu I fragment), #20: line #20-derived total DNA, #40: line #40-derived total DNA, and #49: line #49-derived total DNA.

Next, a PCR fragment (258 bp) specific for the transgene sequence was amplified using the prepared genomic DNA as a template and 2 sets of synthesized primer pairs (A) 5'-GCT CTA GAG CCT CTG CTA ACC-3' (SEQ ID NO: 5) and 5'-TGA ACA GCT CCT CGC CCT TGC TC-3' (SEQ ID NO: 6), and (B) 5'-TGA GCA AAG ACC CCA ACG AGA AGC-3' (SEQ ID NO: 7) and 5'-TTA GCC AGA AGT CAG ATG CTC AAG-3' (SEQ ID NO: 8) (FIG. 2).

EXAMPLE 3

Confirmation of GFP Expression in Individual Transgenic Mouse

To confirm GFP expression in the transgenic mice obtained in Example 2, the forelimbs of an individual mouse were observed immediately after birth under a fluorescence microscope.

Fluorescence of EGFP was visualized under a Carl Zeiss laser scanning confocal microscope (LSM510). EGFP fluorescence was excited with a 488 nm argon-ion laser and imaged through a 505–530 nm bandpass emission filter.

Figure 3:
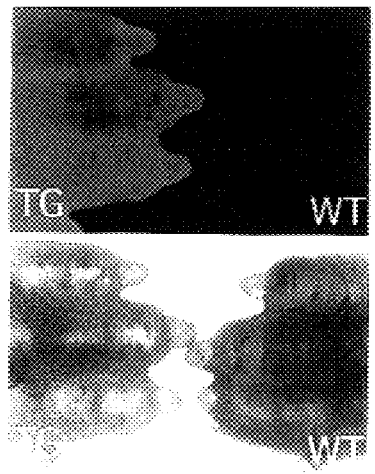
FIG. 3 shows photographs showing GFP expression in the transgenic mouse.

As shown in FIG. 3, fluorescence resulting from GFP expression was observed throughout the forelimbs of the transgenic mouse (Tg) of the present invention. The contours could be distinctly observed as clearly recognized by a comparison with a photograph in a bright field. In contrast, fluorescence was not observed at all for the wild type (WT).

EXAMPLE 4

Confirmation of GFP Expression in the Tissue of the Transgenic Mouse

Mouse testes were isolated from 12-week-old mtGFP-Tg mice, frozen with liquid nitrogen, and then stored in a deep freezer (−80° C.). To prepare 10 μm-thick sections, the frozen testes were sliced using a cryostat at −20° C. and then placed on a slide glass. Fluorescence was observed using a fluorescence microscope.

Figure 4:
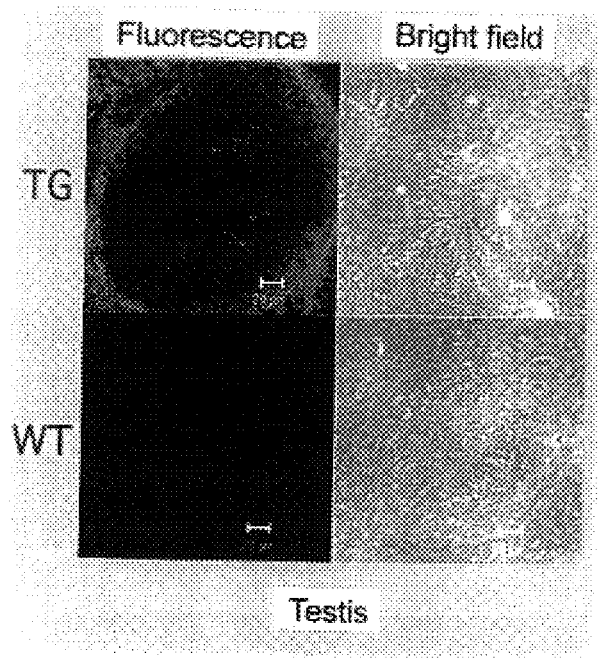
FIG. 4 shows photographs showing GFP expression in the tissue of the transgenic mouse.

As shown in FIG. 4, fluorescence resulting from GFP expression was observed for the transgenic mouse of the present invention. The contours could be distinctly observed as clearly recognized by comparison with a photograph taken in a bright field. In contrast, fluorescence was not observed at all for the wild type (WT).

EXAMPLE 5

Confirmation of GFP Expression in the Fibroblasts of Transgenic Mouse

Primary culture of fibroblasts was performed according to the Explant Culture Method (Fischer SM et al., Methods in Cell Biology (edited by Harris, C. C. et al.) (1980) 21: 207–227, Academic Press, London). The cultured fibroblasts were incubated in DMEM containing 500 nM MitoTracker Red CMXRos (Molecular Probes, OR; cat. M7512) for 15 minutes at 37° C. Then, the stained fibroblasts were washed twice with DMEM and observed using a confocal laser microscope.

Fluorescence of EGFP or MitoTracker Red CMXRos was visualized under a Carl Zeiss laser scanning confocal microscope (LSM510). EGFP fluorescence was excited with a 488 nm argon-ion laser and imaged through a 505–530 nm bandpass emission filter. MitoTracker Red CMXRos fluorescence was excited with a 543 nm HeNe laser and imaged through a 560 nm longpass emission filter.

Figure 5:
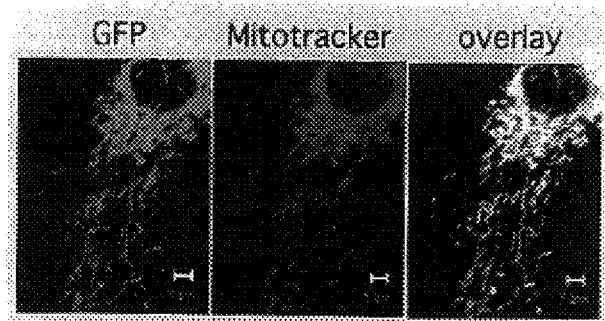
FIG. 5 shows photographs showing GFP expression in the cells of the transgenic mouse.

As shown in FIG. 5, the images by GFP fluorescence and MitoTracker fluorescence almost corresponded to each other.

EXAMPLE 6

Trend in the Early Development Process of Sperm-derived Mitochondria

Sperms, eggs and embryos were collected as we previously described (Kaneda, H. et al., (1995) Proc. Natl. Acad. Sci. U.S.A. 92, 11331–11338). Sperms were prepared as a sperm suspension by extracting the cauda epididymidis from adult mice, and then adding the extract to a TYH medium (Toyota, H. et al., (1971) Jpn J. Anim. Reprod. 16, 147–151). Unfertilized eggs were collected from the oviducts of female mice superovulated by pregnant mare's serum gonadotropin and human chorionic gonadotropin (Hogan, B. et al., (1986) Manipulating the Mouse Embryo: A Laboratory Manual (Cold Spring Harbor Lab. Press, Plainview, N.Y.). Early embryos were collected from the oviducts or uteri of naturally mated mice. A single sperm or a single egg was isolated from the suspension of the sperms or eggs that had been diluted using a capillary for microinjection under a phase contrast microscope, put into 10 μl of distilled water, and then stored at −80° C.

Figure 6:
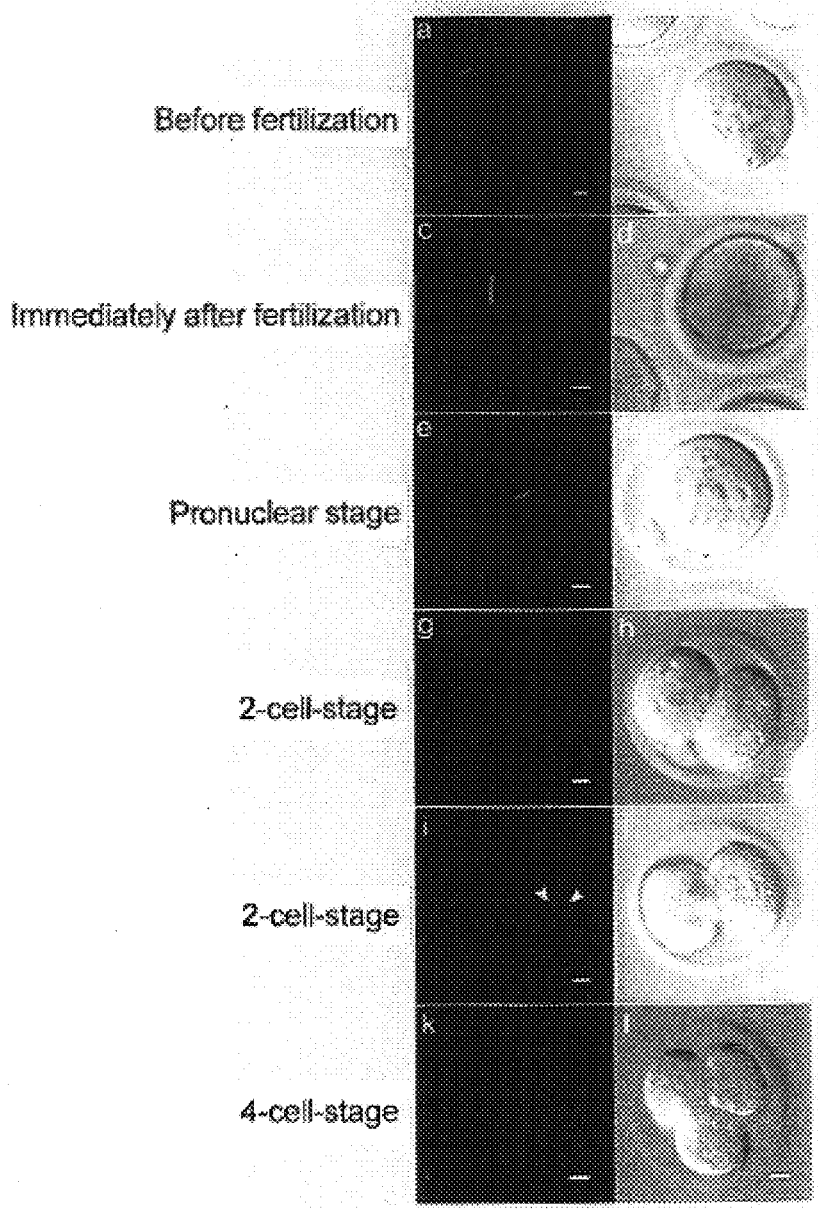
FIG. 6 shows photographs showing the detection of sperm-derived mitochondria in the process of early mouse development.

FIG. 6 shows the detection of sperm-derived mitochondria in the early development process of mouse. "a" and "b" show a sperm and an egg before fertilization. The mitochondria in the middle piece of the sperm were observed as green fluorescence (a: fluorescence and b: bright field). "c (fluorescence)" and "d (bright field)" show an embryo immediately after fertilization. "e (fluoresence)" and "f (bright field)" show a pronuclear-stage embryo. "g (fluorescence)" and "h (bright field)" show a two-cell-stage embryo, and fluorescence of sperm-derived mitochondria was not observed. However, an embryo in which fluorescence remained was observed although at a low rate (i: fluorescence, and j: bright field). "k (fluorescence)" and "l (bright field)" show a four-cell-stage embryo, in which GFP was expressed by the male (sperm)-derived transgene.

EXAMPLE 7

Apoptosis Induction in Mouse Fibroblasts and Observation Thereof

1) Preparation of Cells

Using abdominal skin sections of generated transgenic mice neonates (mtGFP-Tg mice), culture of fibroblasts was begun according to the explant culture method as employed in Example 5. First, the abdominal skin sections of the neonates were cut into approximately a 1 mm square, placed on a plastic dish (FALCON 3001), and then incubated under conditions of 37° C. and 5% $CO_2$ for 15 to 30 minutes. 10% NCS-DMEM (GIBCO, without phenol red) was then added.

On days 7 to 10 after the start of culture, cells were stripped using 0.25% trypsin, and then centrifuged at 700 to 800 g at 4° C. for 5 minutes. The precipitate was resuspended in 10% NCS-DMEM, and then inoculated onto a cover glass (Matunami). One day later, the cells were used for the experiment of apoptosis induction.

2) Apoptosis Induction Method

The medium was exchanged with a medium containing 10% NCS-DMEM and 5 μM staurosporine, the apoptosis inducer.

3 to 5 hours later, cells were observed using a fluorescence microscope (Zeiss, Axiophoto; FITC filter set). In addition, Hoechst 33342, the fluorescent DNA staining reagent (with a final concentration of 200 μM) was added, and then the state of the nuclei was observed.

Figure 7:
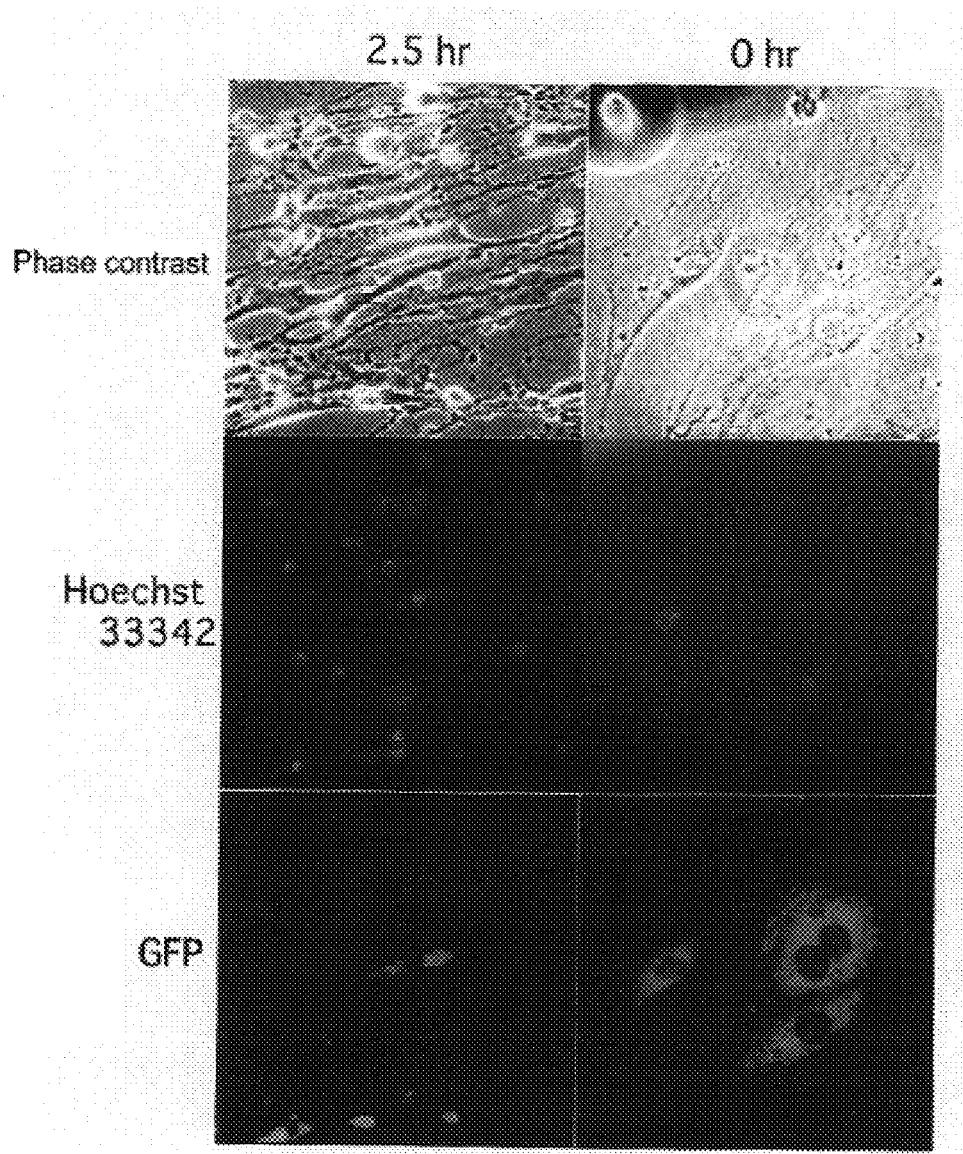
FIG. 7 shows photographs showing the dynamics of mitochondria in mouse fibroblasts on apoptosis induction.

The transgenic mouse-derived fibroblasts were observed before (0 hr) and after (2.5 hr) the addition of staurosporine (FIG. 7). Under a phase contrast microscope, it was observed that the cell slightly changed morphologically after the addition of staurosporine. Further when the morphology of the cell nuclei was observed by Hoechst 33342 staining, chromatin aggregation that is characteristic of cell nuclei undergoing apoptosis was observed. At this time, GFP-labeled mitochondria were observed as existing uniformly in the cytoplasm.

Sequence Listing Free Text
SEQ ID NO: 3: Primer for PCR
SEQ ID NO: 4: Primer for PCR
SEQ ID NO: 5: Primer for PCR
SEQ ID NO: 6: Primer for PCR
SEQ ID NO: 7: Primer for PCR
SEQ ID NO: 8: Primer for PCR
SEQ ID NO: 9: Expression vector pCAGGS-COX8-EGFP
SEQ ID NO: 10: *Aequorea*-derived EFGP coding region modified for codon optimization

INDUSTRIAL APPLICABILITY

The transgenic animal obtained by the present invention expresses GFP, which is observable with its fluorescence, specifically in mitochondria, so that it enables visual capturing of the trend of mitochondria in cells, tissue and animals without any complicated staining process. Further, according to the invention, the degree of color fading is significantly lower than that of dyes which have been conventionally used, enabling sequential observation that has conventionally been impossible. Furthermore, the transgenic animal of the present invention expresses GFP throughout the body, so that it can be used as a supply source of various cells having mitochondria-localized GFP.

Moreover, the present invention also makes it possible to conduct various analyses regarding the localization of mitochondria in each of the tissues and cells of, for example, a pathological model animal, the trend of sperm-derived mitochondria in the early development process, and the dynamics of mitochondria during the apoptosis process.

Further, according to the screening method using the transgenic animal or the cells of the present invention, there is provided a novel method for simply screening for an apoptosis inducer and suppressor. As described above, the present invention has an extremely wide applicable range in the fields of molecular biology and medicine.

What is claimed is:

1. A transgenic mouse whose genome comprises a green fluorescent protein (GFP) gene operably linked to a CAG promoter and a cytochrome c oxidase subunit VIII signal sequence, wherein the GFP is specifically expressed in mitochondria.

2. An isolated tissue or cell derived from the transgenic mouse of claim 1.

3. A screening method for an inducer of apoptosis, comprising the steps of:
   (a) contacting the transgenic mouse of claim 1 or the tissue or cell of claim 2 with a test substance; and
   (b) confirming whether or not apoptosis is induced on the basis of dynamics of mitochondria visualized by GFP.

4. A screening method for an apoptosis suppressor, comprising the steps of:
   (a) contacting the transgenic mouse of claim 1, or the tissue or cell of claim 2 with a test substance;
   (b) treating the mouse or the tissue or cell with the apoptosis inducer; and
   (c) confirming whether or not apoptosis is suppressed on the basis of dynamics of mitochondria visualized by GFP.

5. A method for producing a transgenic mouse whose genome comprises GFP expression specifically in the mitochondria, comprising the steps of:
   (a) introducing an expression vector comprising a GFP gene operably linked to a CAG promoter and a cytochrome c oxidase subunit VIII signal sequence into totipotent cells;
   (b) transferring the totipotent cells obtained in step (a) to the oviduct or uterus of a pseudo-pregnant mouse;
   (c) generating progeny from the pseudo-pregnant mouse of step (b);
   (d) selecting the transgenic strains, which have GFP transgene expression and fluorescence in isolated tissue or cell samples.

6. The transgenic mouse of claim 1, wherein the expression vector comprises the DNA fragment shown in SEQ ID NO:9.

* * * * *